(12) United States Patent
Holsten

(10) Patent No.: US 12,303,167 B2
(45) Date of Patent: May 20, 2025

(54) SURGICAL ACCESS DEVICE WITH ACTIVE SMOKE FILTRATION

(71) Applicant: Covidien LP, Mansfield, MA (US)

(72) Inventor: Henry E. Holsten, Hamden, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/595,922

(22) Filed: Mar. 5, 2024

(65) Prior Publication Data

US 2024/0197364 A1    Jun. 20, 2024

Related U.S. Application Data

(62) Division of application No. 17/178,308, filed on Feb. 18, 2021, now Pat. No. 11,931,072.

(51) Int. Cl.
| | | |
|---|---|---|
| A61B 17/34 | (2006.01) | |
| B03C 3/017 | (2006.01) | |
| B03C 3/12 | (2006.01) | |
| B03C 3/41 | (2006.01) | |
| B03C 3/49 | (2006.01) | |

(52) U.S. Cl.
CPC ...... *A61B 17/3476* (2013.01); *A61B 17/3423* (2013.01); *B03C 3/017* (2013.01); *B03C 3/12* (2013.01); *B03C 3/41* (2013.01); *B03C 3/49* (2013.01); *A61B 2218/008* (2013.01); *B03C 2201/26* (2013.01)

(58) Field of Classification Search
None
See application file for complete search history.

(56) References Cited

U.S. PATENT DOCUMENTS

| | | | |
|---|---|---|---|
| 7,300,448 | B2 | 11/2007 | Criscuolo et al. |
| 7,691,089 | B2 | 4/2010 | Gresham |
| 8,926,508 | B2 | 1/2015 | Hotter |
| 10,617,444 | B2 | 4/2020 | Kellner et al. |
| 10,722,294 | B2 | 7/2020 | Griffiths et al. |
| 11,931,072 | B2 | 3/2024 | Holsten |
| 2017/0164977 | A1 | 6/2017 | Griffiths et al. |
| 2017/0303964 | A1 | 10/2017 | Kellner et al. |
| 2020/0170673 | A1 | 6/2020 | Kellner et al. |
| 2020/0197069 | A1 | 6/2020 | Brewer et al. |

FOREIGN PATENT DOCUMENTS

| | | |
|---|---|---|
| EP | 2456379 B1 | 8/2018 |
| EP | 3744276 A1 | 12/2020 |
| WO | 2017184876 A1 | 10/2017 |
| WO | 2021014316 A1 | 1/2021 |

OTHER PUBLICATIONS

International Search Report and Written Opinion dated May 31, 2022 issued in corresponding PCT Appln. No. PCT/US2022/016724.

*Primary Examiner* — J. Christopher Ball
(74) *Attorney, Agent, or Firm* — Draft Masters IP, LLC

(57) ABSTRACT

A surgical access device includes a housing with an elongate tubular member extending distally from the housing. The elongate tubular member has an open distal aperture. A first electrode is disposed in a first region of the elongate tubular member and circumscribes the elongate tubular member. The first electrode is coupled to an anode of a power supply and is configured to provide airborne particulate matter with a negative electric charge. A second electrode is disposed in a second region of the elongate tubular member and circumscribes the elongate tubular member. The second electrode is coupled to a cathode of a power supply and is configured to attract the airborne particulate matter.

18 Claims, 4 Drawing Sheets

SURGICAL ACCESS DEVICE WITH ACTIVE SMOKE FILTRATION

CROSS-REFERENCE TO RELATED APPLICATION

This application is a divisional of U.S. patent application Ser. No. 17/178,308, filed Feb. 18, 2021, the disclosure of which is incorporated by reference herein in its entirety.

FIELD

The present disclosure generally relates to surgical instruments for accessing a body cavity. In particular, the present disclosure relates to a surgical access device with active smoke filtration for filtering and evacuating smoke and other contaminants generated during performance of a surgical procedure.

BACKGROUND

Minimally invasive surgical procedures including both endoscopic and laparoscopic procedures permit surgery to be performed on organs, tissues and vessels far removed from an opening within the tissue. In laparoscopic procedures, the abdominal cavity is insufflated with an insufflation gas, e.g., $CO_2$, to create a pneumoperitoneum thereby providing access to the underlying organs. A laparoscopic instrument is introduced through a cannula accessing the abdominal cavity to perform one or more surgical tasks. The cannula may incorporate a seal to establish a substantially fluid tight seal about the instrument to preserve the integrity of the pneumoperitoneum.

Instruments utilized during a laparoscopic procedure may include lasers, electro-cautery or sonic cutting instruments, which produce smoke and/or an aerosol as a byproduct of treating tissue. Smoke plumes can obscure the clinician's field of vision and the odor generated is unpleasant. Further, the smoke plume may contain infectious agents which may contaminate the operating arena thereby presenting a danger to operating personnel. The chemical vapor may be irritating to the respiratory tract and also may be carcinogenic. The smoke, noxious fumes, and other gases and vapors can include particulates, bacteria, viral elements, and undesirable odors.

Conventional methodologies for evacuating smoke include using a surgical smoke evacuation device. This device includes a vacuum pump, tubing, and a filter to filter out particulates and microbials and properly dispose of them. A tube is typically attached to the insufflation port of an access cannula and the smoke is ventilated through the filter. However, this arrangement interrupts the surgical procedure requiring the additional steps of disconnecting the insufflation port from the gas source, mounting the filter to the insufflation port and thereafter reconnecting the gas source to reestablish the pneumoperitoneum to continue the surgical procedure. The separate filter also adds an additional component and expense thereby increasing the cost of the underlying procedure.

Removing the smoke, gases and vapors is typically done through a mechanical filtration method. Because the surgical field is a high moisture environment, the filter tends to clog. The clogged filter, and the corresponding reduced flow rate, becomes a limiting factor. It is also desirable not to adversely impact the pneumoperitoneum.

It would be desirable to provide smoke evacuation during surgery in a compact, efficient arrangement that can also reduce cost.

SUMMARY

The present disclosure relates to a surgical access device. The surgical access device includes a housing and an elongate tubular member extending distally from the housing. The elongate tubular member includes an open distal aperture. A first electrode is circumferentially disposed about a first region of the elongate tubular member and is electrically coupled to an anode of a power supply. The first electrode is configured to provide airborne particulate matter with a negative electric charge. A second electrode is circumferentially disposed about a second region of the elongate tubular member that is proximally spaced from the first region of the elongate tubular member. The second electrode electrically is coupled to a cathode of the power supply and configured to attract the airborne particulate matter.

In aspects of the present disclosure, the surgical access device may also include a source of vacuum coupled to the housing for evacuating the airborne particulate matter through the elongate tubular member.

In a further aspect of the present disclosure, the airborne particulate matter may acquire the negative electric charge from the first electrode and may be attracted to the second electrode.

In yet another aspect of the present disclosure, the first and second electrodes may extend circumferentially about an outer surface of the elongate tubular member.

In an aspect of the present disclosure, one of the first or second electrodes may be a flexible mesh.

In another aspect of the present disclosure, the airborne particulate matter may collect on an inner surface of the elongate tubular member proximate the second electrode.

In some aspects of the present disclosure, the power supply may provide an output voltage of about 30k VDC.

The present disclosure also relates to a surgical access assembly having a housing with an elongate tubular member extending therefrom. The elongate tubular member is insertable into a body cavity of a patient. A first electrode is located in a distal region of the elongate tubular member. A second electrode is located in an intermediate region of the elongate tubular member. A power supply has an anode and a cathode. The first electrode is coupled to the anode and the second electrode is coupled to the cathode. Airborne particulate matter in the elongate tubular member acquires a negative charge from the first electrode and is attracted to the second electrode.

In an aspect of the present disclosure, a source of vacuum may be coupled to the housing for evacuating the airborne particulate matter through the elongate tubular member.

In another aspect of the present disclosure, the first and second electrodes may extend circumferentially about an outer surface of the elongate tubular member.

In a further aspect of the present disclosure, one of the first or second electrodes may be a flexible mesh.

In aspects of the present disclosure, the intermediate region may be longitudinally spaced from and proximal of the distal region.

In yet another aspect of the present disclosure, the airborne particulate matter may collect on an inner surface of the elongate tubular member proximate the second electrode.

In an aspect of the present disclosure, the power supply may provide an output voltage of about 30k VDC.

The present disclosure also relates to a method of treating smoke in a surgical site. The method includes inserting an elongate tubular member of a surgical access device into the surgical site. The method also includes performing a surgical procedure in the surgical site that generates smoke with airborne particulate matter. The method further includes supplying a negative electrical charge to a first electrode that is coupled to the elongate tubular member and disposed in a distal region thereof. The method also includes supplying a positive electrical charge to a second electrode that is coupled to the elongate tubular member and disposed in an intermediate region that is proximal of the distal region. The method further includes applying vacuum to a lumen of the elongate tubular member, the vacuum generating a flowpath from the distal region of the elongate tubular member towards a proximal region of the elongate tubular member such that the airborne particulate acquires a negative electrical charge from the first electrode and is attracted to the second electrode.

In aspects of the present disclosure, applying the vacuum to the lumen of the elongate tubular member may include coupling a source of vacuum to a housing of the surgical access device.

In another aspect of the present disclosure, supplying the negative electrical charge to the first electrode may include the first electrode extending circumferentially about an outer surface of the elongate tubular member.

In further aspects of the present disclosure, supplying the positive electrical charge to the second electrode may include the second electrode extending circumferentially about the outer surface of the elongate tubular member.

In yet another aspect of the present disclosure, applying the vacuum to the lumen of the elongate tubular member may include the airborne particulate matter collecting on an inner surface of the elongate tubular member proximate the second electrode.

Other features of the disclosure will be appreciated from the following description.

DESCRIPTION OF THE DRAWINGS

The accompanying drawings, which are incorporated in and constitute a part of this specification, illustrate aspects and features of the disclosure and, together with the detailed description below, serve to further explain the disclosure, in which.

DETAILED DESCRIPTION

Figure 1:
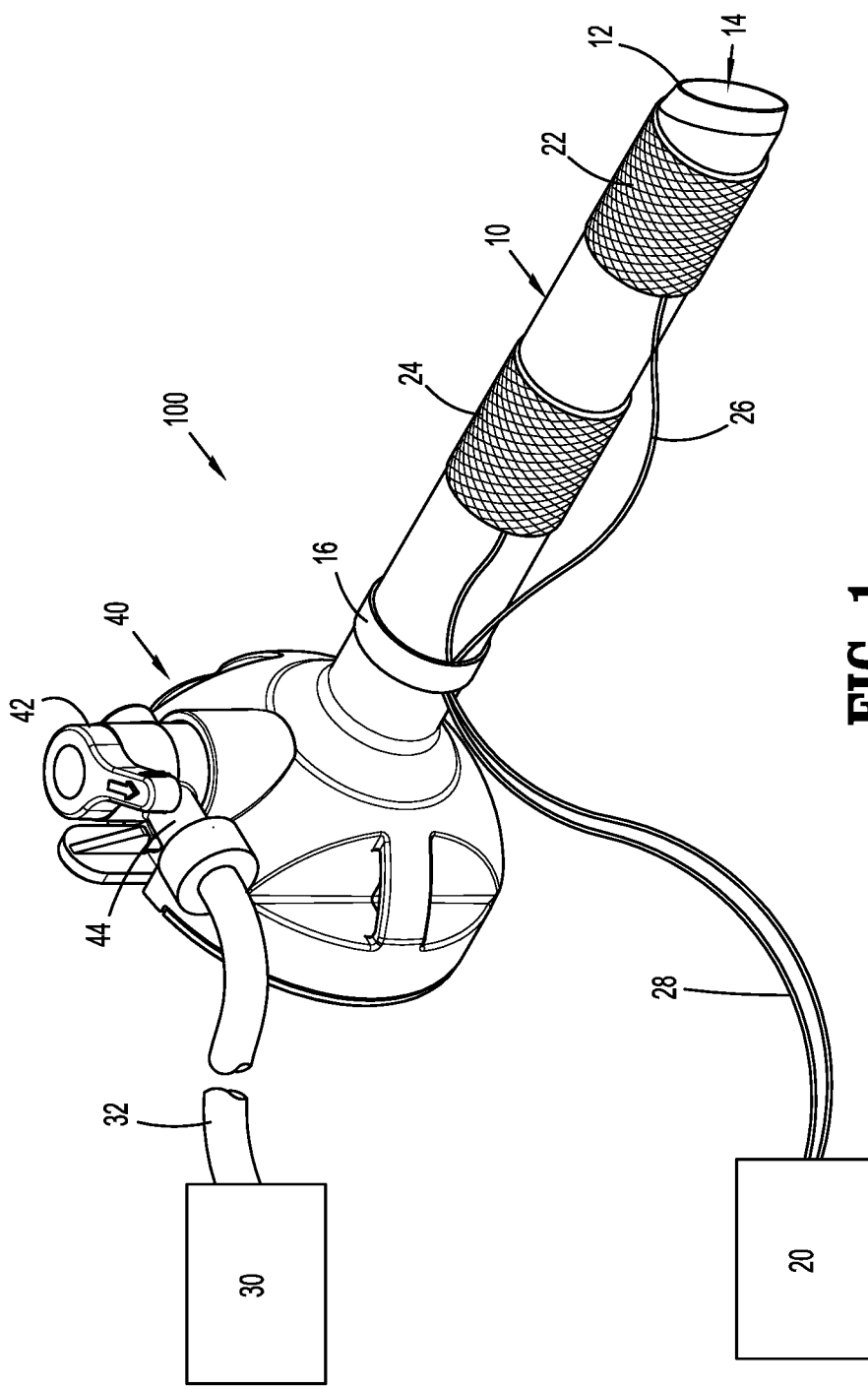
FIG. 1 is a perspective view of a surgical access assembly according to an aspect of the present disclosure.

Aspects of the disclosure are described hereinbelow with reference to the accompanying drawings; however, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Descriptions of technical features of an aspect of the disclosure should typically be considered as available and applicable to other similar features of another aspect of the disclosure. Accordingly, technical features described herein according to one aspect of the disclosure may be applicable to other aspects of the disclosure, and thus duplicative descriptions may be omitted herein. Like reference numerals may refer to like elements throughout the specification and drawings.

Initially, with reference to FIG. 1, a surgical access device is illustrated and referenced generally as surgical access device 100. The surgical access device 100 includes a housing 40 disposed at a first or proximal end with an elongate tubular member or cannula 10 extending from a distal end of the housing 40. The surgical access device 100 will be described to the extent necessary to disclose aspects of the present disclosure. For a detailed description of the structure and function of components of exemplary surgical access devices, reference may be made to U.S. Pat. Nos. 7,300,448; 7,691,089; and 8,926,508, the entire content of each of these patents is hereby incorporated by reference. The cannula 10 has a distal aperture 12 and a proximal aperture (not shown) that define a lumen 14 through the cannula 10 that is configured to receive a shaft 52 of a surgical instrument 50 (FIG. 2) therethrough.

A first plate or electrode 22 is located in a distal region of the cannula 10 and is proximate the distal aperture 12. The first electrode 22 generally circumscribes the cannula 10. A second plate or electrode 24 is located in an intermediate region of the cannula 10, which is located between the distal region and a proximal region when the cannula 10 is attached to the housing 40. Similar to the first electrode 22, the second electrode 24 generally circumscribes the cannula 10. It is envisioned that the first and second electrodes 22, 24 may only extend part way around an outer circumference of the cannula 10. One or both of the first and second electrodes 22, 24 may be a wire, a mesh, a flexible conductive circuit, an electrically conductive organic compound, or combinations thereof. The first and second electrodes 22, 24 have external insulation minimize the risk of conducting electricity to body tissue in a body cavity "BC" (FIG. 3) or surgical site.

A power supply 20 is usable with the surgical access device 100. The power supply 20 is a high voltage DC power supply that receives an input voltage between 2-12 VDC and has an output voltage between 5k VDC to 90$k$ VDC. An anode of the power supply 20 (i.e., the negative terminal) is electrically coupled to the first electrode 22 via a first wire 26 and a cathode of the power supply 20 (i.e., the positive terminal) is electrically coupled to the second electrode 24 via a second wire 28. It is contemplated that the polarities of the first and second electrodes 22, 24 may be reversed with the first electrode 22 coupled to the cathode of the power supply 20 and the second electrode 24 coupled to the anode of the power supply 20. The first and second wires 26, 28 extend proximally along the cannula 10 towards the housing 40 and under a band 16 that is positioned near the proximal end of the cannula 10. The band 16 maintains the first and second wires 26, 28 in position along an outer surface of the cannula 10 such that the first and second wires 26, 28 may be generally flush with the outer surface of the cannula 10.

This minimizes the risk of the first and second wires 26, 28 from catching on objects, including body tissue, present in the surgical site.

Additionally, with continued reference to FIG. 1, a source of vacuum 30 is attachable to the surgical access device 100. Specifically, the source of vacuum 30 has a hose 32 extending therefrom and a distal end of the hose is connected to a port 44 of a valve 42 located on the housing 40 of the surgical access device 100. With the valve 42 in the open position, the source of vacuum 30 is able to draw air into the open distal aperture 12 of the cannula 10 from the surgical site. The air, along with any particulate matter suspended in the air (i.e., airborne particulate matter), travels through the cannula 10, through the valve 42, and into the hose 32 prior to reaching the source of vacuum 30.

Figure 2:
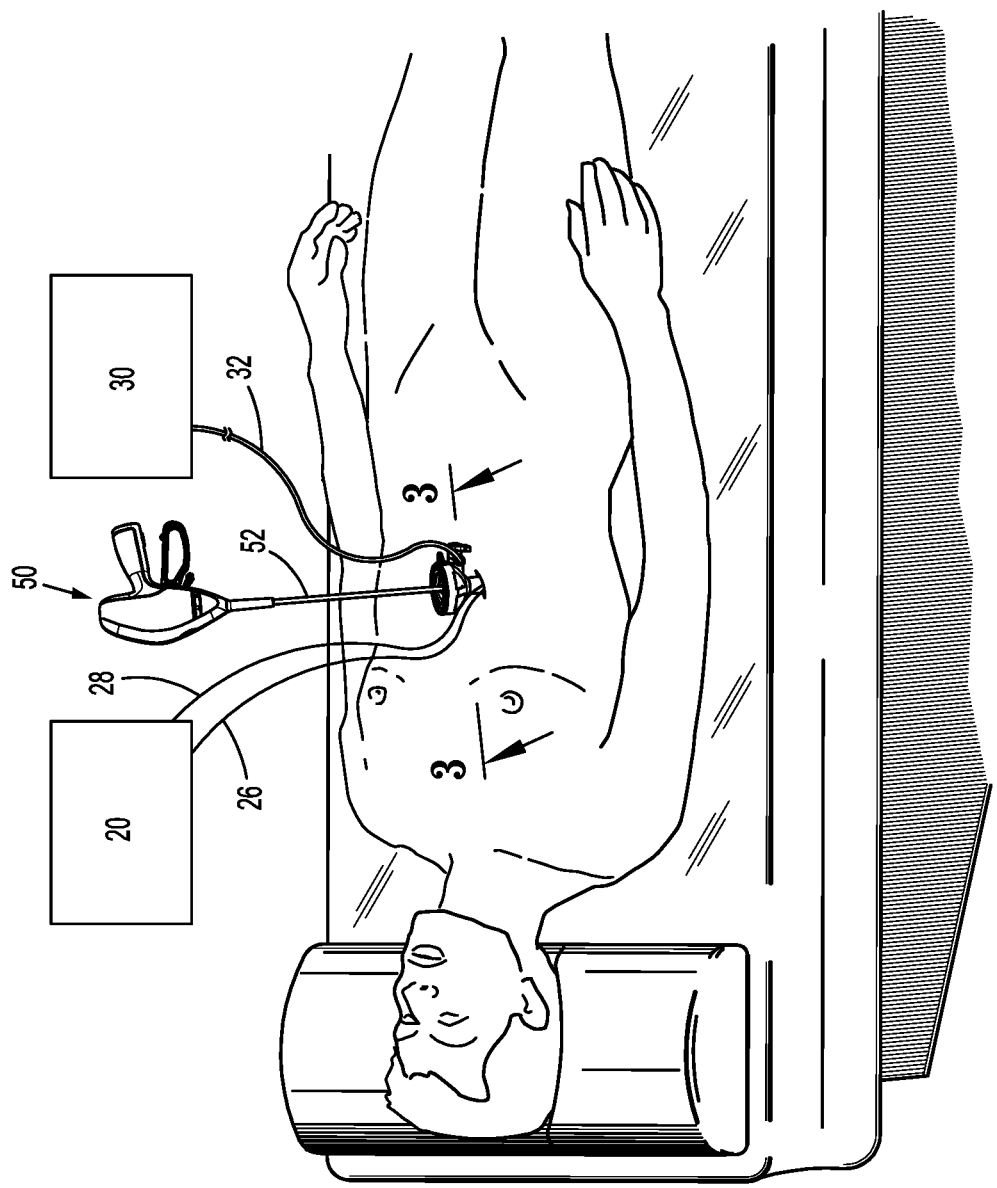
FIG. 2 is a perspective view of the surgical access assembly of FIG. 1 inserted into a patient with a surgical instrument inserted into a surgical access device of the surgical access assembly.
Figure 3:
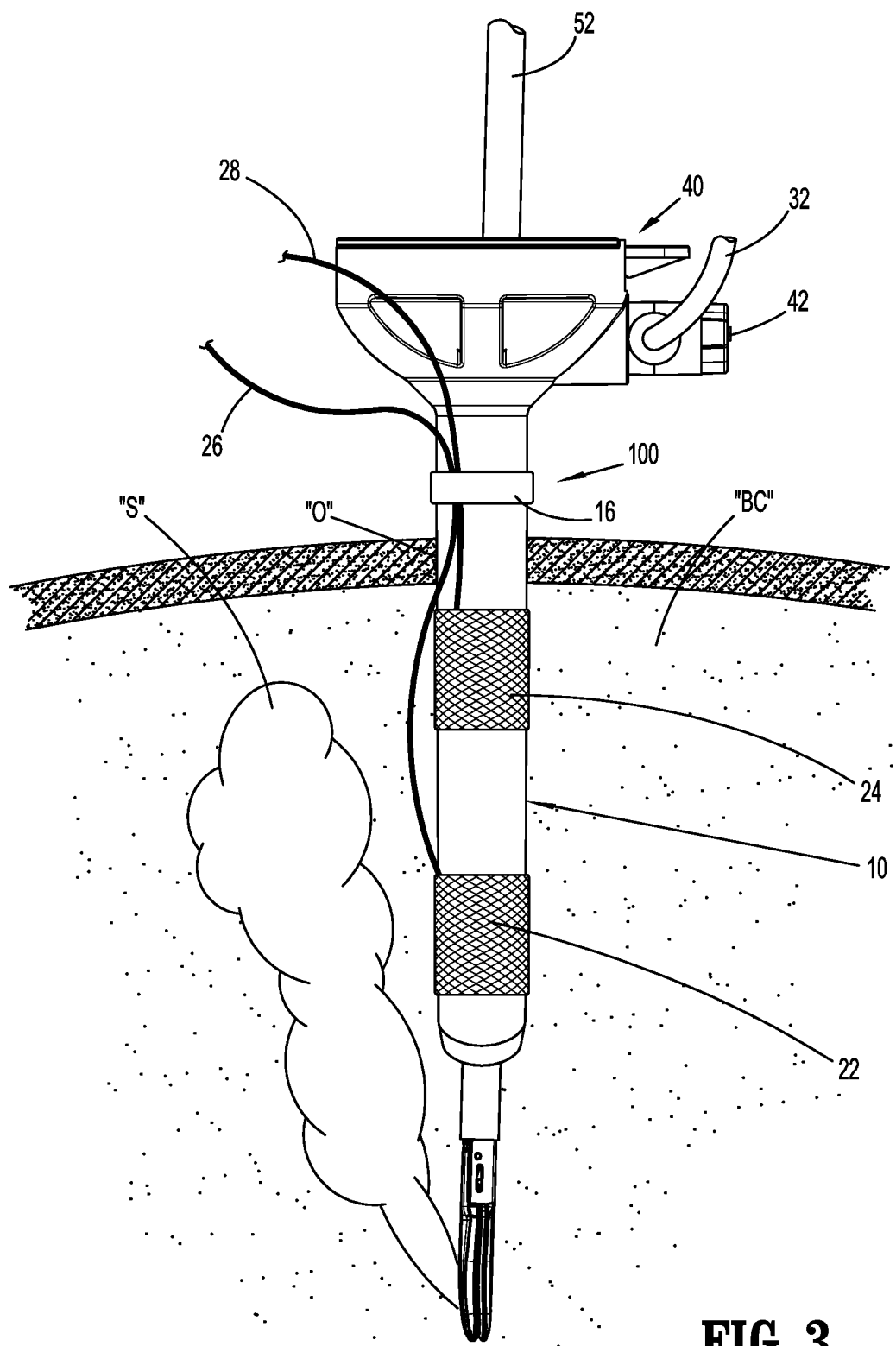
FIG. 3 is a side view of the surgical access device and surgical instrument of FIG. 2 inserted into a body cavity of the patient showing a plume of smoke in the body cavity.

With additional reference to FIG. 2, the surgical access device 100 is positionable through an opening "O" (FIG. 3) in a patient's skin to access an underlying surgical site in the patient's body cavity "BC" (FIG. 3). The power supply 20 is electrically coupled to the first and second electrodes 22, 24 via the first and second wires 26, 28 respectively. The source of vacuum 30 is fluidly coupled to the lumen 14 of the cannula via the hose 32 that is connected to the port 44 of the valve 42 on the housing 40 of the surgical access device 100. The shaft 52 of the surgical instrument 50 is inserted through the housing 40 and into the cannula 10 of the surgical access device 100. The surgical instrument 50 is an endoscopic instrument. The surgical instrument 50 may be a clip applier, a grasper, a dissector, a retractor, a stapler, a laser probe, an imaging device (e.g., an endoscope or a laparoscope), an electro-surgical device, and the like.

As shown in FIG. 3, the surgical access device 100 is inserted through the opening "O" in the patient's tissue and into the body cavity "BC" to provide access to the surgical site. When the cannula 10 is positioned in the body cavity "BC", the first and second electrodes 22, 24 are located below the surface of the skin. The shaft 52 of the surgical instrument 50 is inserted through the surgical access device 100 to perform a surgical procedure in the surgical site. As shown, the surgical instrument 50 is an electro-surgical instrument that generates smoke including airborne particulate matter "S" during the surgical procedure. Safely and effectively removing the smoke and airborne particulate matter "S" helps maintain visibility in the surgical site and protects the health of personnel involved in the surgical procedure. Smoke and airborne particulate "S" matter remain in the body cavity "BC" due to the interaction between the shaft 52 of the surgical instrument 50 and the seal assembly (not shown) in the housing 40 of the surgical access device 100.

Figure 4:
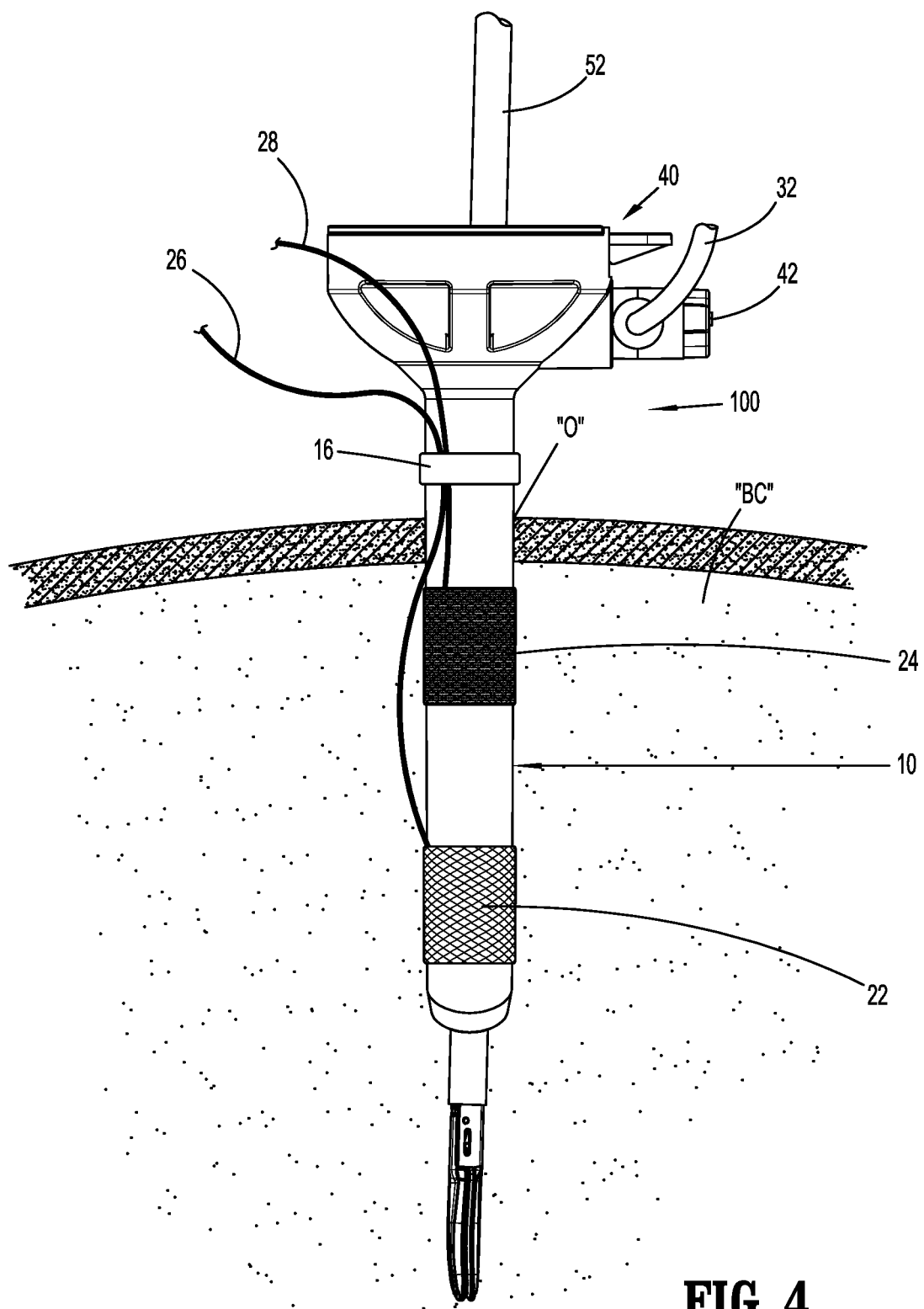
FIG. 4 is a side view of the surgical access device and surgical instrument of FIG. 3 showing airborne particulate collecting on an electrode.

Referring now to FIG. 4, smoke and the attendant airborne particulate matter "S" is removed from the surgical site in the body cavity "BC" by applying a vacuum to the surgical site from the source of vacuum 30. The vacuum applied to the cannula 10 creates a negative pressure in the cannula 10 relative to the pressure present in the body cavity "BC". This pressure differential causes the smoke and airborne particulate matter "S" to flow from the surgical site in the body cavity "BC" through the open distal aperture 12 into the cannula 10 and towards the source of vacuum 30. The first electrode 22 that is coupled to the anode of the power supply 20 creates a first electric field around the first electrode 22 having a negative charge and the second electrode 24 that is coupled to the cathode of the power supply 20 creates a second electric field around the second electrode 24 having a positive charge. As the smoke and airborne particulate matter "S" transit through the cannula 10, it first passes through the first electric field where the airborne particulate matter is ionized by the negative charge present in the first electric field thereby acquiring a generally negative charge. As the ionized airborne particulate matter flows through the cannula 10, it passes into the second electric field that has a positive electric charge. The oppositely charged airborne particulate matter is attracted by the positive electric charge and accumulates on an inner wall of the cannula 10 in the vicinity of the second electrode 24. Evacuating the smoke and airborne particulate matter "S" may be done in parallel with a surgical procedure, following a surgical procedure, or a combination of the two.

By subjecting the airborne particulate matter to a negative electric field and ionizing the airborne particulate matter with a negative electric charge, the oppositely charged electrode easily attracts and retains the ionized airborne particulate matter thereby preventing the airborne particulate matter from exiting the body cavity "BC" into the environment surrounding the patient (e.g., an operating room). This arrangement is as efficient as using a mechanical filtration device to separate out the airborne particulate matter. It is contemplated that the electrical fields may be reversed with the first electrode 22 coupled to the cathode of the power supply 20 such that a positive electric field is generated in the vicinity of the first electrode 22 and that the second electrode 24 would be coupled to the anode of the power supply 20 such that a negative electric field is generated in the vicinity of the second electrode 24. In this instance, the airborne particulate matter would acquire a positive electric charge as it transits through the cannula 10 past the first electrode 22 and is attracted to the negative electric field near the second electrode 24 where the airborne particulate matter would accumulate.

It is contemplated that the first and second electrodes may be affixed to a shaft of a laparoscopic surgical instrument such as the shaft 52 of the surgical instrument 50 that is depicted in FIG. 2. It is also envisioned that the first and second electrodes may be affixed to a wand that is insertable through a lumen of a cannula such as the lumen 14 of the cannula 10 as shown in FIG. 1. In either instance, the principles of operation remain the same with one electrode ionizing the airborne particulate matter and the other electrode attracting the ionized airborne particulate matter.

Persons skilled in the art will understand that the devices and methods specifically described herein and illustrated in the accompanying drawings are non-limiting. It is envisioned that the elements and features may be combined with the elements and features of another without departing from the scope of the disclosure. As well, one skilled in the art will appreciate further features and advantages of the disclosure.

What is claimed is:

1. A method of evacuating smoke at a surgical site using a surgical access device, the method comprising:
    providing an elongate tubular member defining a lumen configured to receive a surgical instrument;
    creating a negative electrical charge within the lumen near a first region of the elongate tubular member to apply a negative electrical charge within the lumen in the first region;
    creating a positive electrical charge within the lumen near a second region of the elongate tubular member proximally of the first region;
    creating a vacuum within the lumen of the elongate tubular member to generate an air flow having airborne particulate matter within the lumen of the elongate tubular member that moves from the first region of the elongate tubular member towards the second region of the elongate tubular member to move the airborne particulate matter towards the second region;

ionizing the airborne particulate matter as it passes in a proximal direction through the lumen in the first region; and accumulating the ionized airborne particulate matter on an inner wall of the lumen in the second region.

2. The method of claim 1, wherein creating the vacuum within the lumen of the elongate tubular member includes coupling a source of vacuum to a housing of the surgical access device.

3. The method of claim 1, wherein creating the negative electrical charge includes creating the negative electrical charge circumferentially about an outer surface of the elongate tubular member.

4. The method of claim 3, wherein creating the positive electrical charge includes creating the positive electrical charge circumferentially about the outer surface of the elongate tubular member.

5. The method of claim 1, wherein creating the vacuum within the lumen of the elongate tubular member causes the airborne particulate matter to enter the lumen through a distal aperture thereof.

6. The method of claim 1, wherein creating the negative electrical charge comprises coupling a first electrode to a power source, the first electrode located in the first region of the elongate tubular member.

7. The method of claim 6, wherein creating the positive electrical charge comprises coupling a second electrode to the power source, the second electrode located in the second region of the elongate tubular member.

8. The method of claim 7, wherein the first electrode is disposed circumferentially about an outer surface of the elongate tubular member in the first region, and the second electrode is disposed circumferentially about an outer surface of the elongate tubular member in the second region.

9. A method of removing airborne particulate matter from a flow of air, the method comprising:

creating a flow of air within a lumen of an elongate tubular member, the flow of air comprising airborne particulate matter that enters a distal aperture of the lumen and moves from a distal region of the elongate tubular member towards a proximal region of the elongate tubular member;

creating a negative electrical field near a distal region of the elongate tubular member;

ionizing the airborne particulate matter as it moves in a proximal direction through the distal region; and creating a positive electrical field proximally of the negative electrical field to collect the ionized airborne particulate matter on an inner wall of the lumen of the elongate tubular member.

10. The method of claim 9, wherein creating the flow of air within the lumen of the elongate tubular member includes applying a vacuum to the lumen of the elongate tubular member.

11. The method of claim 9, wherein creating the negative electrical field includes coupling a first electrode supported about the elongate tubular member to an anode of a power supply.

12. The method of claim 9, wherein creating the positive electrical field includes coupling a second electrode supported about the elongate tubular member to a cathode of a power supply.

13. The method of claim 9, wherein the lumen is defined between a proximal aperture and the distal aperture and is configured to receive a surgical instrument.

14. A method of evacuating smoke in a surgical site comprising:

providing a surgical access device comprising an elongate tubular member with a lumen ending at a distal aperture;

supplying a negative electrical charge to a first electrode, the first electrode coupled to an outer surface of the elongate tubular member in a distal region thereof;

supplying a positive electrical charge to a second electrode, the second electrode coupled to the outer surface of the elongate tubular member in an intermediate region that is proximal of the distal region; and applying a vacuum to the lumen of the elongate tubular member, the vacuum generating an air flow comprising airborne particulate from the distal region of the elongate tubular member towards a proximal region of the elongate tubular member such that the airborne particulate acquires a negative electrical charge from the first electrode as it moves proximally toward the second electrode.

15. The method of claim 14, wherein applying the vacuum to the lumen of the elongate tubular member includes coupling a source of vacuum to a housing of the surgical access device.

16. The method of claim 14, wherein applying the vacuum to the lumen of the elongate tubular member includes causing the airborne particulate matter to move past the second electrode and collect on an inner surface of the elongate tubular member proximate the second electrode.

17. The method of claim 14, wherein the first electrode comprises a wire, a mesh, a flexible conductive circuit, or an electrically conductive compound.

18. The method of claim 14, wherein the lumen is defined between a proximal aperture and the distal aperture and is configured to receive a surgical instrument.

* * * * *